United States Patent [19]

Betzing

[11] 4,235,793

[45] Nov. 25, 1980

[54] PROCESS TO OBTAIN OILY, HIGHLY PURIFIED PHOSPHATIDYLCHOLINES

[75] Inventor: Hans Betzing, Horrem, Fed. Rep. of Germany

[73] Assignee: A. Nattermann & Cie. GmbH, Cologne, Fed. Rep. of Germany

[21] Appl. No.: 899,525

[22] Filed: Apr. 24, 1978

[30] Foreign Application Priority Data

Apr. 27, 1977 [DE] Fed. Rep. of Germany ..... 27187979

[51] Int. Cl.$^3$ ............................ A23J 7/00; C07F 9/02; C11C 3/00
[52] U.S. Cl. ................................ 260/403; 260/412.4; 260/412.8; 260/428.5
[58] Field of Search ................. 260/403, 412.4, 123.5, 260/412.8, 428.5

[56] References Cited

U.S. PATENT DOCUMENTS

| | | | |
|---|---|---|---|
| 2,945,869 | 7/1960 | Meyer | 260/403 |
| 3,544,605 | 12/1970 | Betzing | 260/403 |

Primary Examiner—John F. Niebling
Attorney, Agent, or Firm—Burns, Doane, Swecker & Mathis

[57] ABSTRACT

An improved process for obtaining highly purified phosphatidylcholines (lecithin) including a high content of essential fatty acids is disclosed. Raw lecithins are first extracted with a lower alcohol of 1 to 3 carbon atoms. The resulting two phases are separated and the alcohol-rich upper phase is treated with an aluminum oxide adsorbent. Elution of the adsorbent with an alcohol (as in known processes) results in an oily phosphatidylcholine, free of cephalin and inositol phosphatides but possessing a high content of essential fatty acids.

5 Claims, No Drawings

PROCESS TO OBTAIN OILY, HIGHLY PURIFIED PHOSPHATIDYLCHOLINES

German Pat. No. 1,617,679 discloses a process to obtain highly purified phosphatidylcholine (lecithin) with a high content of essential fatty acids from plant lecithins by adsorption of the phosphatides on aluminum oxide and extraction with alcohol. This process is characterized in that the raw oil phosphatides are dissolved in ethyl acetate or a dichlorinated hydrocarbon having 1 to 2 carbon atoms or in mixtures of these solvents. The solvent can contain up to 6% by volume of alcohol. The solution is then treated, with stirring, with at least a five-fold amount of aluminum oxide relative to the content of raw phosphatide. Finally, the highly purified phosphatidylcholine is liberated with alcohol from the separated aluminum oxide. According to German Pat. No. 1,617,680 the solution of the oily raw phosphatide solution is contacted with an aluminum oxide column (instead of stirring therewith) and the chemically pure phosphatidylcholine is liberated from the aluminum oxide adsorbent with alcohol.

Swiss Pat. No. 361,088 and U.S. Pat. No. 2,945,869 describe purification processes to obtain soya phosphatide fractions to be used as emulsifiers for aliphatic emulsions designed for intravenous application. Alcoholic solutions of previously deoiled raw phosphatides are treated according to these processes with $Al_2O_3$, MgO or activated charcoal, respectively in order to make these solutions poor in cephalin and, primarily, to remove from these solutions most of the inositol-containing phosphatides which were found to lower the blood pressure in cats when introduced intravenously.

However, this latter process always requires a previous deoiling of the commercially available raw phosphatides prior to the preparation of the alcoholic solutions which will only lead to a reduction in the cephalin content, regardless of the adsorbent being used. A more extensive or a complete removal of the cephalin can not be accomplished by this known process.

German Pat. No. 1,053,299, assigned to the assignee of the present application, discloses a process to obtain natural choline phosphoric acid diglyceride esters which are free of colamin phosphoric acid diglyceride esters, by use of column chromatography where aluminum oxide is used, among other substances, as the adsorbent. This process again uses an alcoholic extract of the previously deoiled raw phosphatide, with the prior deoiling accomplished by repeated extractions with acetone.

In the case of the processes disclosed by German Pat. Nos. 1,617,679 and 1,617,680, the oily raw phosphatide mixtures are dissolved in ethyl acetate or a chlorinated hydrocarbon without prior deoiling, and these solutions are then treated with aluminum oxide. Deoiling of the raw phosphatides occurs while all phosphatides will remain at the adsorbent. The phosphatidylcholine (lecithin) can then be selectively liberated by treating the aluminum oxide with an alcohol. Highly purified oil-free phosphatidylcholines can be obtained by means of this process.

Unexpectedly and surprisingly, it has now been found that it is not necessary to treat the oily raw phosphatides with ethyl acetate or dichlorinated hydrocarbons and that it is possible to extract the raw phosphatide with lower alcohols having 1 to 3 carbon atoms, then to treat this extract directly with the aluminum oxide and finally, as described by the above-mentioned German Pat. Nos. 1,617,679 and 1,617,680, to liberate the adsorbed phosphatide with alcohol from the aluminum oxide.

In contrast thereto, the process proposed by the invention makes it possible to obtain phosphatidylcholines with a high content of essential fatty acids in the molecule together with the vegetable oil contained in the raw phosphatide. Experience has shown that it becomes very often necessary to produce oily solutions of highly purified phosphatidylcholines. This is true especially in the pharmaceutical field when it is desired to apply highly purified phosphatidylcholines orally, for example, in the form of gelatine capsules. Recent resorption studies using phosphatidylcholine marked with radioactive substances have shown that oral application of an oily preparation of phosphatidylcholine with primarily polyunsaturated fatty acids will increase the resorption several times in comparison with a watery preparation.

Natural vegetable oils, always associated with the phosphatides, such as sunflower or soya oil, preferably intermixed with mono- and di-glycerides which were prepared from the same oils, are particularly suitable oily substances. It becomes thus possible directly to obtain a fluid, that is, pourable phosphatidylcholine fractions, which are often very useful in other fields of application, for example cosmetics and dietetics.

The preparation of a pourable oily solution of highly purified phosphatidylcholine to be filled into gelatine capsules is presently accomplished by again mixing the oilfree phosphatidylcholine obtained by the process described in the German Pat. No. 1,617,679 with the natural vegetable oil obtained in the course of the purification or with some other edible oil, possibly with the further admixture of monoglycerides or free fatty acids. However, this mode of preparation necessitates removal of the oil attached to the phosphatide mixtures prior to or during the adsorption process at the $Al_2O_3$ in order to eliminate the cephalin and the inositol phosphatides.

The prior art processes as well as that according to German Pat. No. 1,053,299 or its patent of addition, in addition to being relatively uneconomical, have several disadvantages. First, in the course of deoiling of the commercially available raw phosphatides with acetone there will always form small quantities of mesityl oxide which is chemically produced by the assemblage of two acetone molecules. Mesityl oxide has very adverse effects due to its toxicity and its characteristic, specific odor, even in very minute quantities. Second, during the chromatographic fractionation of oil and phospholipid, there are always formed solvent mixtures which require fractional distillation prior to their reuse.

In one embodiment, the present invention provides a process for obtaining oily, highly purified phosphatidylcholines from oily raw phosphatides comprising extracting an oily phosphatide extract from the oily raw phosphatide with a lower alcohol, directly contacting the said oily phosphatide extract with an aluminum oxide adsorbent and recovering the adsorbed phosphatidylcholine therefrom. There is also provided the product of this process.

The process proposed by the present invention is performed by first extracting with methanol, ethanol or propanol at temperatures up to 50° C. the commercially available raw lecithins, still containing approximately 20 to 40% of oil. The two phases which form during the cooling of the mixture are separated from each other by suitable techniques, for example by decanting or centrifuging. The alcohol-rich upper phase is then treated with the aluminum oxide, either with stirring or by passing through a chromatographic column filled with the adsorbent. Elution with the alcohol results in an oily phosphatidylcholine, free of cephalin and inositol phosphatides but possessing a high content of essential fatty acids.

It was unexpected, and contrary to the teaching of the present state of art, that an oily alcoholic phosphatide solution would be suitable without any pre-treatment for a chromatographic separation on aluminum oxide, and where the high oil-content of the solution does not interfere in any manner with the adsorption of the acid phosphatides. These circumstances are especially surprising in view of the poor solubility of oil in alcohol which could be expected to cause a separation of the oil from the phosphatide phase during contact with the aluminum oxide, and thus a blockage of the active centers of the adsorbent. It was further to be expected that adsorption of the phosphatidylcholine from the alcoholic solution would not take place to a sufficient extent as in the previously known processes this solvent was used as the element.

The oily alcoholic extracts utilized for the process of the present invention can be prepared by treating the raw phosphatides once or several times with alcohol at temperatures up to the boiling point of the solvent, and most advantageously at temperatures between 20° and 50° C. The phase mixture obtained thereby can be separated either by decanting or by centrifuging. After treating the alcoholic upper phase with aluminum oxide with stirring, the adsorbent, being separated from the solution, is then stirred for several minutes together with ethanol and then isolated in a decanter. The rinsing can be repeated by use of a small amount of ethanol and the aluminum oxide which will now hold the undesirable accompanying lipids is discarded or reprocessed. If a chromatographic column is used for the separation of the acid phospholipids, the oily phosphatidylcholine concentrates are obtained by eluting the column with alcohol, preferably ethyl alcohol. If necessary, it is also possible to reduce the oil content in the phosphatidylcholine fraction by fractionating the eluate flowing from the column.

The alcoholic solutions so obtained in accordance with the process, either after stirring with aluminum oxide or after the column chromatography, are then liberated from the solvent under vacuum and under the protection of an inert gas. If desired, the solutions may be filtered. A small amount of a filter aid such as diatomaceous earth products sold commercially under the trademark Celite may also be used. The yield is a very pure oily fraction of natural phosphatidylcholine which is free, or almost free of cephalin, its content of essential fatty acids ranging from 66 to 70% and above.

Suitable for the extraction of the oily raw phosphatides and for carrying out the chromatographic process of the invention are the lower alcohols having 1 to 3 carbon atoms, preferably ethyl alcohol. The alcohol may be utilized in mixture with small quantities of water with the solution containing from 85 to 96% by weight of alcohol (and concomitantly from 15 to 4% of water), the latter concentration being particularly advantageous since it is commercially used and available.

Basic and neutral aluminum oxides, and preferably basic aluminum oxides of the activity grade 1-3 as standardized according to Brockmann, can be used as adsorbents.

The process proposed by the invention makes it thus possible to liberate oily phosphatide fractions from cephalin and inositol phosphatide by a simple treatment with aluminum oxide either in a chromatographic column or by stirring, while conserving the oily phase and also to prepare oily phosphatidylcholine fractions with a high content of essential fatty acids by use of one single processing step.

The products of the process proposed by the invention have, due to their high phosphatidylcholine content of more than 90% of the phosphatide fraction and a content of more than 70% of essential fatty acids relative to all fatty acids present, a valuable therapeutic effect on the metabolism for various illnesses, such as arteriosclerosis, diabetes and hyperlipidaemia, even if applied orally at very low doses, such as 2 grams a day, the effectiveness of the products being due among other effects to the lowering of pathologically raised blood-fat level.

The highly purified oily phosphatidylcholine fractions, obtained from regular raw phosphatides in accordance with the above-described process, have the following typical composition:

Iodine number: 95–105
Oil content: 15–30%
Total phosphorus: 2.4–2.75%
Choline: 9.5–10.8%
phosphorous : choline molar ratio: 0.996%

Gas-chromatographic analysis of the fatty acids shows the following average values:

| | (a) oily phosphatidylcholine fraction according to the invention | | (b) deoiled phosphatidylcholine fraction | |
|---|---|---|---|---|
| | from soya phosphatide | from sunflower phosphatide | soya | sunflower |
| $C_{16}$ | 13.7% | 9.8% | 15.0% | 10.0% |
| $C_{18}$ | 3.0% | 4.0% | 3.3% | 3.5% |
| $C_{18:1}$ | 13.0% | 14.0% | 10.0% | 14.0% |
| $C_{18:2}$ | 63.5% | 72.2% | 65.5% | 72.5% |
| $C_{18:3}$ | 6.8% | — | 6.2% | — |

The invention is additionally illustrated in connection with the following Examples which are to be considered as illustrative of the present invention. It should be understood, however, that the invention is not limited to the specific details of the Examples.

EXAMPLE 1

(a) Preparation of the oily ethanolic sunflower-phosphatide solution.

1 kg of raw sunflower phosphatide with an oil content of 35% is stirred for one hour with 5 liters of ethanol under a nitrogen atmosphere at 40° C. The solution is left standing for one hour at room temperature and the ethanol-rich upper phase of light specific weight is then separated from the viscous lower phase in a separating funnel.

(b) Treatment with $Al_2O_3$.

1.5 liters of the above-obtained upper phase having solids content of 75 gram, and 30 gram of sunflower oil are vigorously stirred together with 300 gram of $Al_2O_3$ for 2.5 hours at room temperature and under a $N_2$ protective atmosphere. When the adsorbent settles, the ethanol solution is decanted off and the Al₂O₃ is rinsed twice, in each case with 150 ml of ethanol. The two ethanol solutions are filtered off together after the admixture of 1 gram of Celite as a filter aid and the solvent is distilled off in the vacuum under nitrogen at a bath temperature of 40° C. Yield: 45 gram of a viscous, oily phosphatidylcholine fraction which is practically free of cephalin and which has the following composition:
Oil content: 30%
phosphatidyl-choline content: 64%

EXAMPLE 2

1 liter of an upper phase, prepared from raw soyabean phosphatide by ethanol extraction as described in Example 1(a), with a solids content of 53 gram and containing 27% of soya oil, is stirred vigorously together with 280 gram of Al₂O₃ for four hours under an inert gas atmosphere. When the adsorbent settles, the ethanol solution is separated, the Al₂O₃ is rinsed twice with 150 ml of ethanol in each case and the combined ethanolic extracts are finely filtered with the admixture of Celite. After evaporation of the solvent in vacuum under nitrogen protection, there remains 33 gram of a pliable yellowish phosphatidylcholine fraction which is free of cephalin and which can be transformed into a pourable form by the admixture of oil or partial glycerides with over 50% of unsaturated fatty acids. The recovered fraction has the following composition:
Soya oil: 25%
phosphatidyl-choline content: 68%.

EXAMPLE 3

1.3 liter of a 4.1% ethanolic soya-phosphatide solution of 28% solids content, obtained as the upper phase or the ethanol extraction of oily raw soyabean phosphatide at 25° C. using the procedure of Example 1, is introduced under N₂ protection into a chromatographic column of 31 mm diameter and 400 mm height which is filled with a suspension of 280 gram of Al₂O₃ in ethanol. After the passage of the solution, the adsorbent is then rinsed with 350 ml of alcohol. The combined ethanol extracts are liberated from the solvent in the vacuum under inert gas protection and at a bath temperature of 40° C. Yield: 35 gram (68%) of a highly purified phosphatidylcholine fraction which is completely free of cephalin and which has an oil content of 29% and a phosphatidylcholine content of 70%.

EXAMPLE 4

400 gram of soyabean raw phosphatide are twice extracted for 30 minutes at 40° C. using 1,000 ml of methanol in each case. The combined methanol extracts, after cooling to room temperature, have a solids content of 9%, an oil content of 12% and a phosphatidylcholine content of 33%.

One liter of this methanolic solution is introduced, under the protection of an inert gas, into a chromatographic column which is filled with a 500 gram suspension of aluminum oxide. Following the passage of the solution, the adsorbent at the column is then rinsed with 700 ml of methanol. The combined methanol eluates are concentrated in the vacuum at 40° C. under the protection by an inert gas.

The yield: 55 gram of a yellow, plastic product, entirely free of cephalin with an oil content of 30% and a phosphatidylcholine content of 66%. After the admixture of mono-diglycerides containing more than 50% of unsaturated fatty acids, there is being obtained a pourable, oily phosphatidylcholine concentrate.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for obtaining oily, highly purified phosphatidylcholines from oily raw phosphatides comprising extracting an oily phosphatide extract from the oily raw phosphatide with a solvent selected from the group consisting of lower alcohols and aqueous solutions thereof containing from about 85 to 96 percent alcohol, directly contacting the said oily phosphatide extract with an aluminum oxide adsorbent and recovering the adsorbed phosphatidylcholine therefrom.

2. The process of claim 1 wherein the lower alcohol is ethyl alcohol.

3. The process of claim 1 wherein the adsorbed phosphatidylcholine is recovered by liberation with alcohol.

4. The process of claim 1 wherein said oily phosphatide extract is obtained by mixing the oily raw phosphatide with said lower alcohol at a temperature up to 50° C. to obtain a two-phase system including an oily phosphatide phase substantially free of cephalin and inositol phosphatide and separating the two phase system to recover the said oily phosphatide phase as said extract.

5. The process of claim 1 wherein the oily raw phosphatides are derived from soya or sunflowers.

* * * * *